United States Patent [19]
Poveromo

[11] Patent Number: 4,840,565
[45] Date of Patent: Jun. 20, 1989

[54] TOOTH-DIE DOWEL-PIN AND LOCKING ASSEMBLY AND METHOD OF MAKING A DENTAL MODEL INCORPORATING SAID ASSEMBLY

[76] Inventor: Melvin D. Poveromo, 14135 N. Miami Ave., North Miami, Fla. 33161

[21] Appl. No.: 131,787

[22] Filed: Dec. 11, 1987

[51] Int. Cl.$^4$ .............................................. A61C 19/00
[52] U.S. Cl. ...................................................... 433/74
[58] Field of Search ................ 433/74, 225, 220, 221

[56] References Cited

U.S. PATENT DOCUMENTS

| | | |
|---|---|---|
| 2,851,728 | 9/1958 | Spalten et al. .................... 433/74 |
| 2,851,728 | 9/1958 | Spalten et al. . |
| 3,413,725 | 12/1968 | Stern et al. . |
| 3,454,256 | 7/1969 | Stern et al. . |
| 3,521,354 | 7/1970 | Stern et al. . |
| 3,896,548 | 7/1975 | Zahn . |
| 4,056,585 | 11/1977 | Waltke . |
| 4,139,943 | 2/1979 | Dragan . |
| 4,457,709 | 7/1984 | Moore . |

Primary Examiner—Robert Peshock
Attorney, Agent, or Firm—Sughrue, Mion, Zinn, Macpeak & Seas

[57] ABSTRACT

A dowel-pin for a tooth-die has two longitudinally spaced bore holes into which are inserted corresponding pins of a U-shaped locking device to form an assembly which is embedded in the base stone during the fabrication of a dental model. After trimming of the stone, the locking device is removed to permit a corresponding tooth die to be removed from the model. When the tooth die is returned to the model, the locking device is reinserted through the stone and into the bore holes of the dowel-pin, thereby locking the tooth die and dowel-pin against movement in all directions.

13 Claims, 8 Drawing Sheets

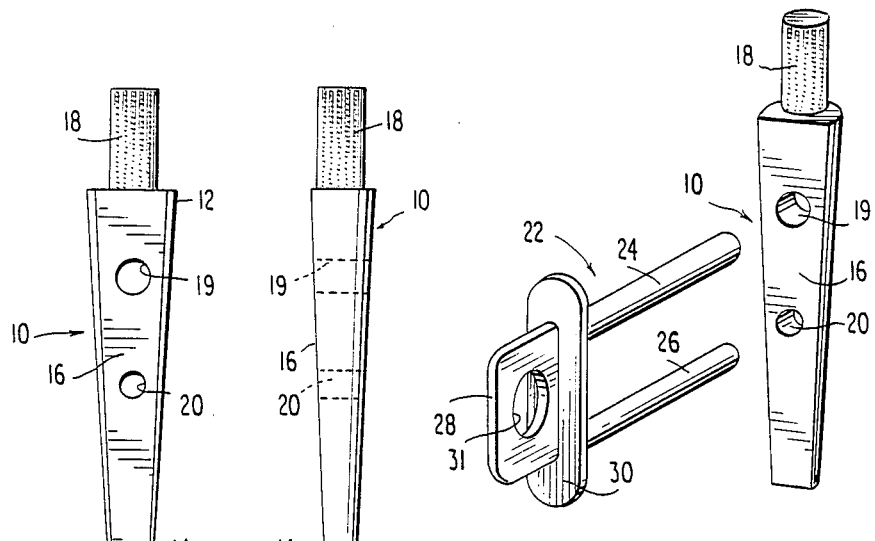
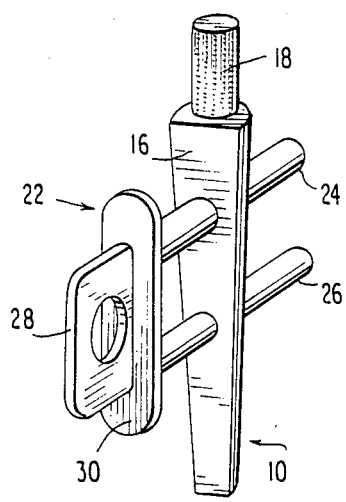
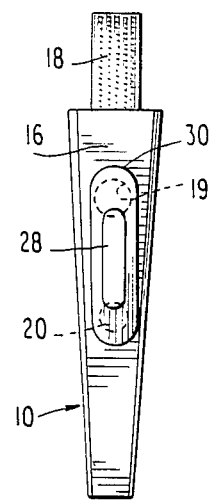
FIG.1A  FIG.1B  FIG.1C
FIG.1D  FIG.1E

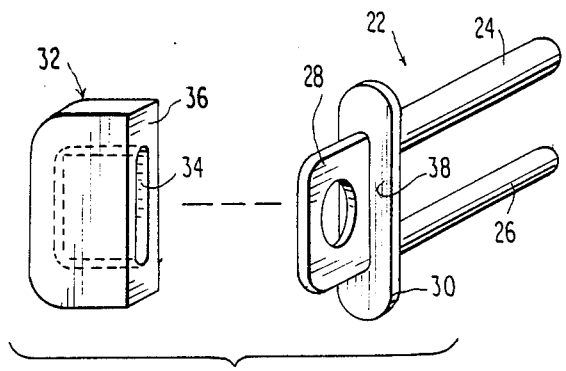
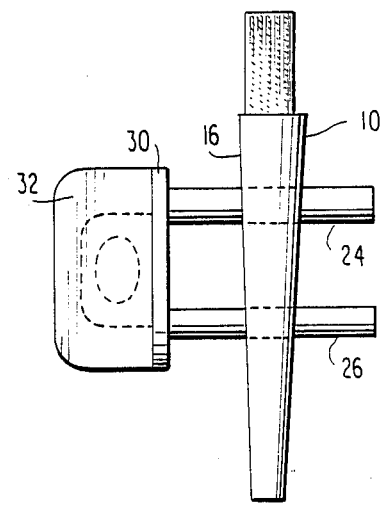
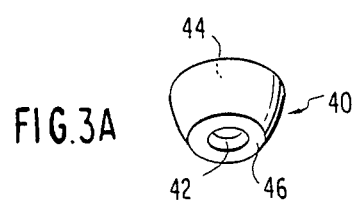
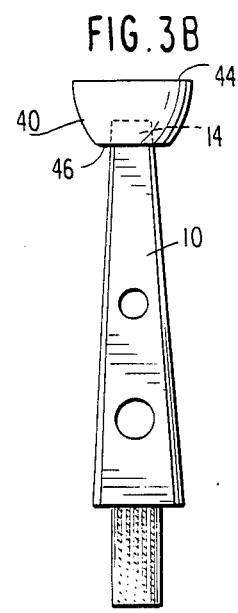
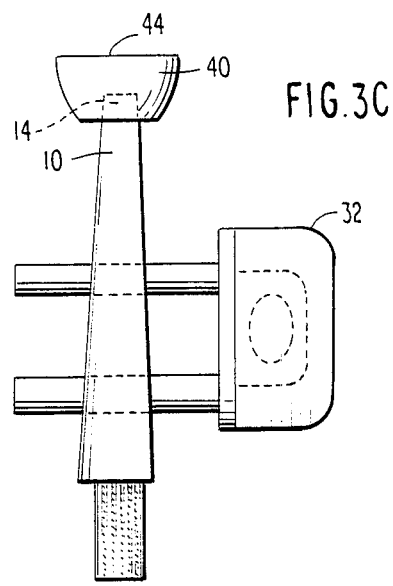

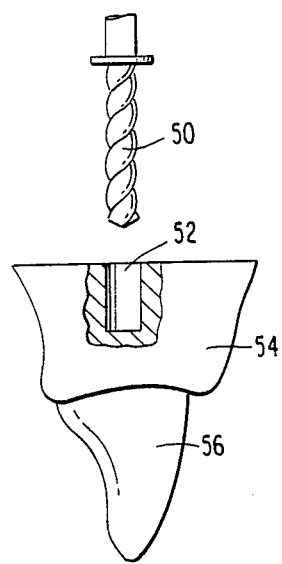
FIG. 4A
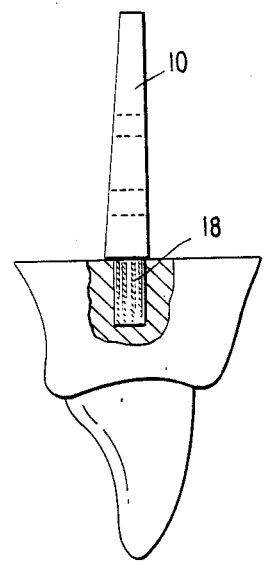
FIG. 4B
FIG. 4C
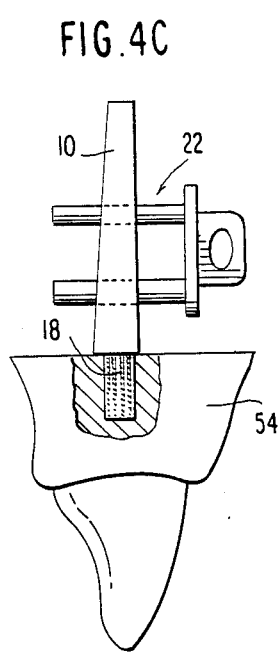
FIG. 4D
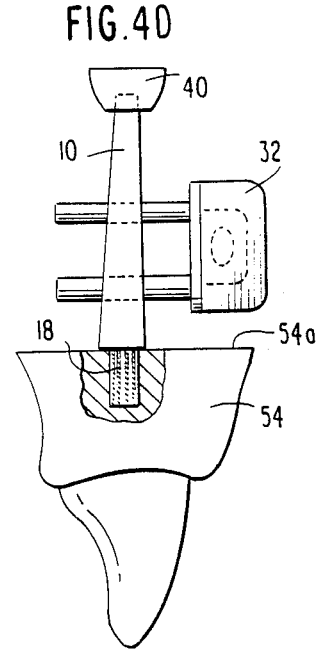

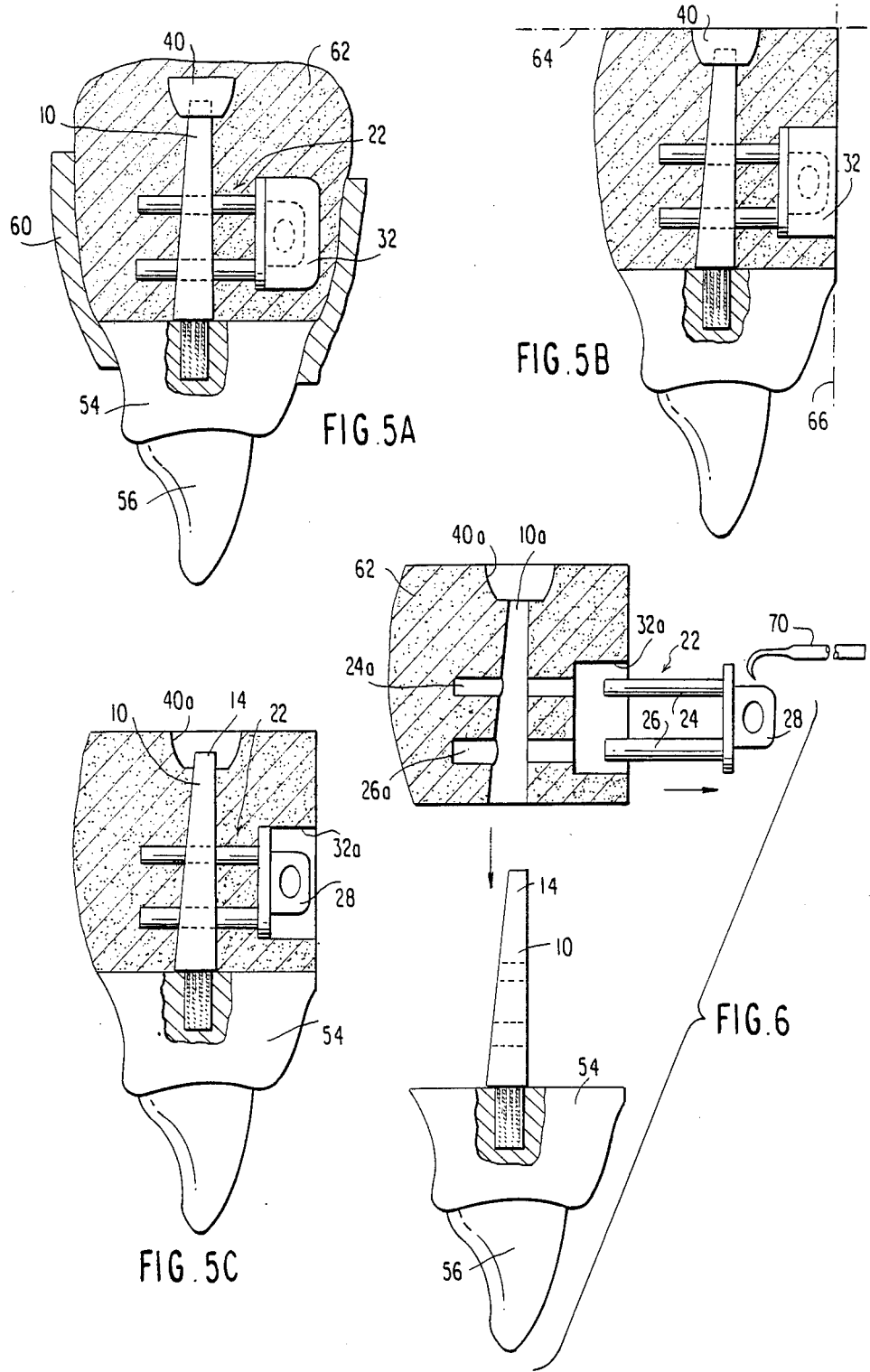

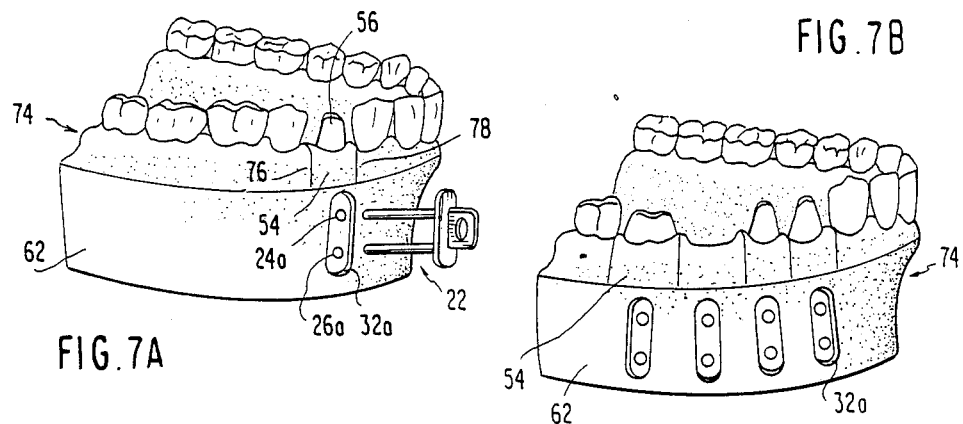
FIG. 7A
FIG. 7B
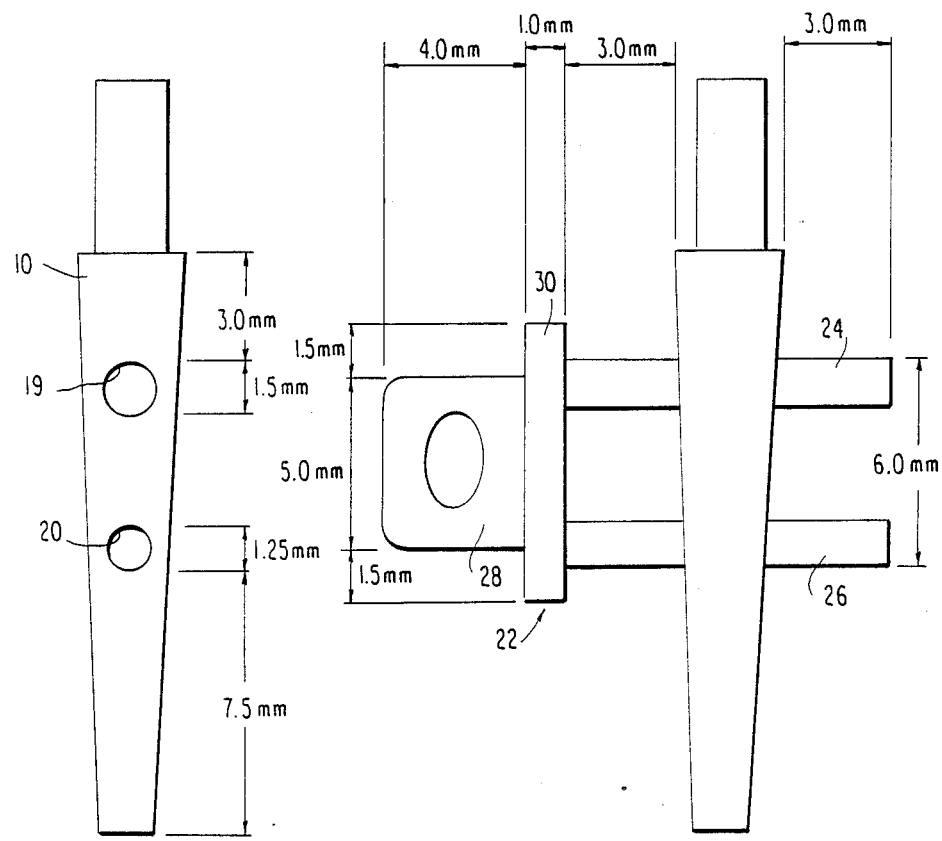
FIG. 8A
FIG. 8B

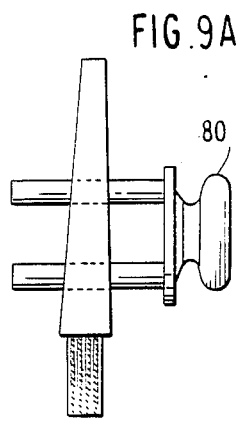 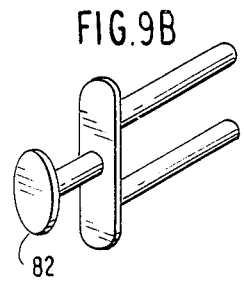 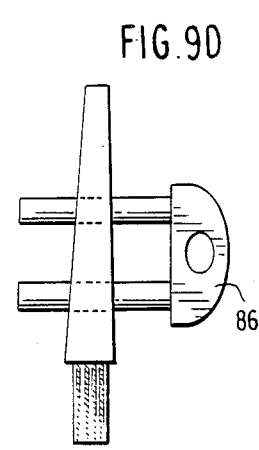 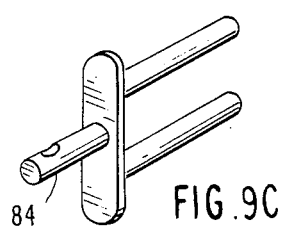 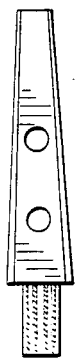 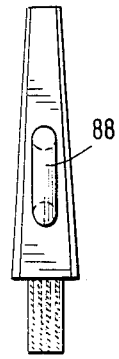 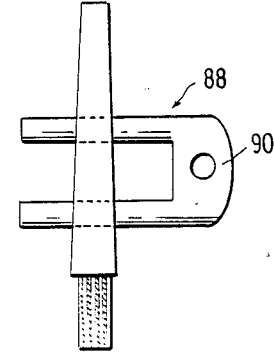 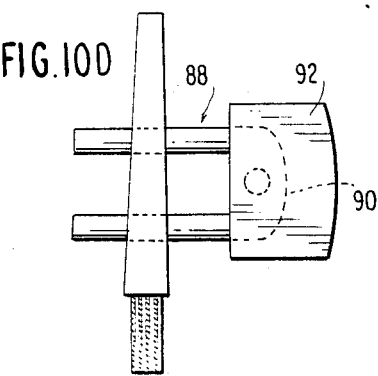 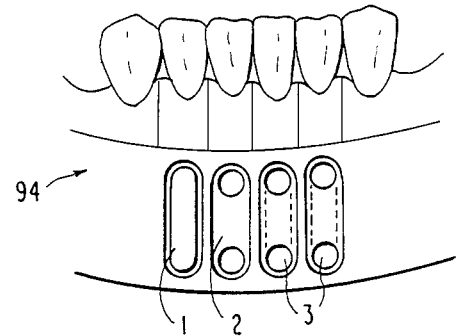

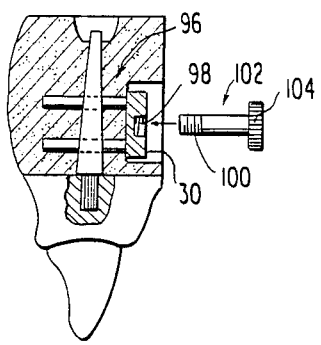
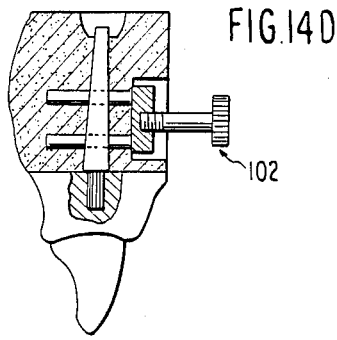
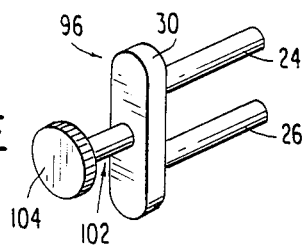
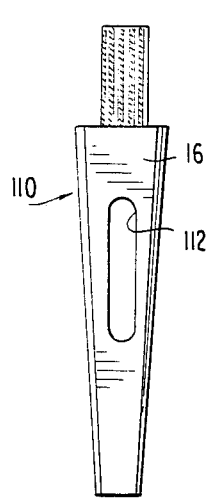
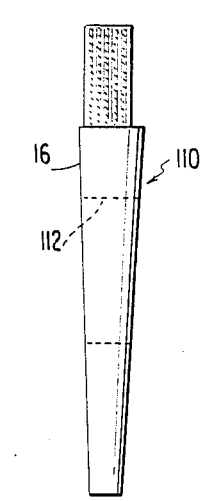
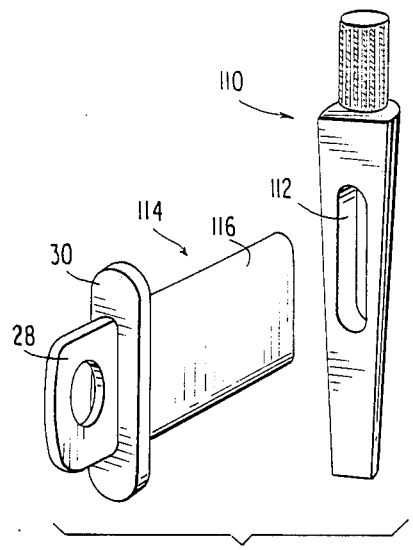
FIG.15A  FIG.15B  FIG.15C

TOOTH-DIE DOWEL-PIN AND LOCKING ASSEMBLY AND METHOD OF MAKING A DENTAL MODEL INCORPORATING SAID ASSEMBLY

BACKGROUND OF THE INVENTION

1. Field of the Invention

My invention relates generally to the field of dental models and, more particularly, to a novel dowel-pin and locking assembly for a tooth die and to a method of making a dental model incorporating such an assembly.

2. Description of the Prior Art

In order to fabricate a crown or inlay on a tooth, an impression of a patient's mouth is taken, and a reproduction is made in the dental laboratory. Since the reproduction is a solid positive model of the mouth, it is necessary to isolate reproductions or dies of the individual teeth which have been prepared to receive a restoration. This isolation is accomplished by various types of dowel pins, each of which is secured to a respective die by either a first known process wherein a dowel-pin is inserted into the impression material before the dental model is fabricated, or a second known process wherein the entire solid dental model is first made and, then, holes are drilled above the individual prepared tooth areas or dies to receive individual dowel pins which are inserted and glued into the drilled holes.

In the fabrication of dental models and individual tooth dies, it is extremely important to have both an accurate reproduction of each tooth die and also of the relationship between each individual die and the adjacent model teeth. Since the natural teeth that are positioned in the dental arch are stationary, each individual die on the dental model must be accurately positioned with respect to the entire model so as to correspond to the natural teeth. If there is any movement of the die in the model, then the fabrication of a dental restoration (crown, inlay, etc.) will not be accurate, because, then, the model will not be an accurate reproduction of the natural teeth.

Furthermore, when individual crowns are to be fabricated to restore two or more natural teeth and are to be intentionally joined (soldered) on the model, any movement of the die or dies will cause the final restoration to be inaccurate since the movement of the dies creates an inaccurate reproduction of the natural teeth. Similarly, when crowns are fabricated on dies, and removable appliances are fabricated to be inserted on or into these crowns, any movement of the dies would produce an inaccurate restoration for obvious reasons.

The prior art is replete with various types of dowel pins for incorporation into each individual die. For example, there are (a) single vertical dowel pins with tapers, (b) double vertical pins and (c) single and double vertical pins with corresponding sleeves that are embedded into the stone model. In each case, the intention is to isolate each individual die, and the purpose of the single or double vertical pins is to prevent movement of the die on the master model. Since each die, with its inserted dowel-pin, rests upon the base of the dental model, and since this base has a flat surface, the only security of the die is the vertical dowel that penetrates into the base. As a result, a fulcrum or pivoting effect commonly occurs since there is nothing to prevent the vertically extending conventional dowel-pin from moving. As a result of this fulcrum effect, the die can move in five directions: bucally; lingually; mesially; distally; and also upwardly since there is also nothing available to prevent upward movement of the dowel-pin. Furthermore, often the die bottom that rests upon the flat base surface of the dental model is rough, broken or contains debris that prevents the die from properly seating on the surface of the model base. As a result, and in addition to the fulcrum effect of such a vertical dowel-pin, there is produced an inaccuracy in the relationship of the die to the model and, consequently, an inaccuracy in the fabrication of any restoration which is to be installed on the natural teeth. In addition, since dental models are not standard, and since tooth lengths are not standard, it is often necessary to have an extremely long die. Furthermore, dental models may be of different thicknesses. As a result, it should be clear that, as the length of the die increases, or as the thickness of the dental model increases, the so-called fulcrum effect of the die and dowel-pin also increases. Since there is no standard length of die or model, the conventional dowel-pin or pins do not prevent movement of the die relative to the model.

A pre-examination search of the prior art revealed many U.S. patents relating to means for positioning the dowel-pin when making a dental model according to the first process cited above, i.e., a process wherein the dowel-pin is positioned within a negative impression which is then filled with dental material or plaster which surrounds and embeds the dowel-pin, as opposed to the second process (with which my invention is associated) wherein the entire negative impression is filled with dental material or plaster to produce a positive master casting or model into which holes are selectively drilled for receiving subsequently inserted dowel-pins.

U.S. Pat. No. 2,851,728 shows a dental dowel-pin having a single hole therein for receiving an elongated, rod-like repositioning gauge supported in the base stone of a dental model; thus, there is no provision for preventing the above-mentioned fulcrum effect. Furthermore, the single rod-like gauge passes through more than one dowel-pin, a construction which has limited practical value compared to an individual locking device for each dowel pin.

U.S. Pat. Nos. 3,413,725; 3,454,256; and 3,521,354 merely disclose dowel-positioning systems, and also show the use of channel forming members located on the end of a dowel-pin to form a channel in the base stone for facilitating the removal of a selected tooth die from the stone.

U.S. Pat. No. 4,457,709 shows a coiled wire rod for holding a dowel-pin in position in a dental cavity of a tooth impression during the pouring of dental die casting material into the cavity.

U.S. Pat. No. 3,896,548 shows a dental model provided with horizontal wedges which are inserted in mating sockets spanning the parting lines between adjacent tooth dies for maintaining alignment of the tooth dies within the model.

U.S. Pat. Nos. 4,056,585 and 4,139,943 show dowel-pin constructions for use in a dental die.

SUMMARY OF THE INVENTION

Therefore, a primary object of my invention is to provide a tooth-die dowel-pin and locking assembly including a removable and re-insertable locking pin for interacting with the dowel-pin of an individual tooth die for locking the die in a dental model against movement in all directions.

Another object is to provide such an assembly in which machinable plastic locating caps are placed on ends of the dowel-pin and locking pin so that these ends can be located during trimming of the model without any damage to either the dowel-pin or the locking pin.

A further object is to provide a method of installing such an assembly during the fabrication of a dental model and of subsequently using the locking pin.

In summary, in the preferred embodiment, a master dental cast is first fabricated from a dental impression of a patient's mouth. A hole is drilled in the base of each model tooth for which a dental restoration is to be made. One end of a dowel-pin is inserted and glued inside the hole. The dowel-pin has two longitudinally spaced-apart circular holes therein. The two cylindrical pins of a generally U-shaped locking device are transversely inserted through the holes, and dental material for a dental model is poured thereover, thereby embedding the assembled dowel-pin and locking pin in the model. During trimming of the model, plastic locating caps on ends of the dowel-pin and locking device are first engaged by the trimmer, after which the caps are removed to permit access to the ends of the dowel-pin and locking device. After sawing, the locking device is removed from the model to permit the individual tooth die also to be removed. When the die is returned to the model, the locking device is inserted through the model and through the two holes in the dowel-pin of the tooth die, thereby assuring accurate positioning of the tooth die within the model and locking the tooth die against movement in all directions.

BRIEF DESCRIPTION OF THE DRAWING

FIGS. 1A to 1E are different views of a preferred embodiment of the dowel-pin locking assembly of my invention;

FIGS. 2A and 2B are different views showing an optional feature of my invention;

FIGS. 3A to 3C are different views showing another optional feature of the preferred embodiment of my invention;

FIGS. 4A to 4D are various views showing initial steps of a preferred method of making a dental model in accordance with a preferred embodiment of my invention;

FIGS. 5A to 5C show additional steps of the preferred method of my invention;

FIG. 6 illustrates the manner in which the preferred embodiment of my locking assembly is removed from a dental model;

FIGS. 7A and 7B illustrate my invention as its relates to a dental model;

FIGS. 8A and 8B illustrate typical dimensions of a dowel-pin and locking assembly according to my invention;

FIGS. 9A to 9D illustrate additional embodiments of the dowel-pin and locking assembly of my invention;

FIGS. 10A to 10E are different views illustrating another preferred embodiment of the dowel-pin and locking assembly of my invention;

FIGS. 14A to 14E are various views illustrating still another preferred embodiment of my invention; and FIGS. 15A to 15C are different views illustrating still another embodiment of my novel dowel-pin and locking assembly.

DETAILED DESCRIPTION OF THE PREFERRED EMBODIMENTS

Figure 11A:
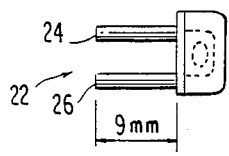
FIGS. 11A, 11B and FIGS. 12A, 12B illustrate a comparison of two different embodiments of the dowel-pin and locking assembly of my invention.

FIG. 1A to FIG. 1E illustrate different views of a preferred embodiment of my novel tooth-die dowel-pin and locking pin assembly. FIGS. 1A and B illustrate the shape of a conventional dowel-pin 10 which is seen to taper inwardly from its fastening end 12 to its free end 14. It has a cross-sectional shape in the form of a circle with a flat side 16. Formed on its fastening end 12 is a knurled portion 18 of reduced diameter for insertion into a drilled hole in the base of a tooth die (as will be described below). Such dowel pins are traditionally made of brass but may be made of any other suitable metal or rigid plastic.

In accordance with my invention, two cylindrical bore holes 19 and 20 are formed at a distance from one another and centered on the longitudinal axis of the dowel-pin 10. In this preferred embodiment, bore hole 19 is of slightly larger diameter than bore hole 20, but they may be of the same diameter. The bore holes are longitudinally spaced apart intermediate the ends 12 and 14 of the dowel-pin.

FIG. 1C shows both the novel dowel-pin 10 and the novel locking device 22 of my novel assembly. The locking device 22 is generally U-shaped and has two parallel longitudinal legs or pins 24 and 26 which are spaced apart by the same distance separating the bore holes 19 and 20 and have substantially the same diameters as the bore holes 19 and 20, respectively, thereby assuring a snug fit when the pins 24, 26 are inserted in the bore holes 19, 20. The U of the locking device is completed by an extension 28 on its pulling end, and a planar flange 30 is interposed between the extension and the legs 24, 26. Formed in the extension 28 is a hole 31 for receiving a suitable instrument to remove or pull the locking device from the dowel-pin. FIGS. 1D and 1E are perspective and front views, respectively, showing the locking device 22 inserted in the dowel-pin 10. The locking device 22 may also be made of brass or any other suitable metal or rigid plastic.

FIGS. 2A and 2B illustrate another feature of the invention in wherein a disposable locating cap 32 is inserted over the extension 28 and into an engagement with the outer surface of the flange 30. Cap 32 has a recess 34 which enables the cap 32 snugly to fit over the extension 28 so that the inner surface 36 of the cap engages the other surface 38 of the flange 30. Cap 32 serves as a locating means for the locking device 22 during trimming of the dental model in which the locking device is embedded along with the dowel-pin. Cap 32 is made of a relatively soft machinable material such as nylon.

FIGS. 3A, 3B and 3C show a locating cap 40 which is attached to the free end 14 of the dowel-pin 10 and which serves the same purpose as the cap 32. That is, during trimming of the model, the trimmer first engages the cap 40 which is, then, removed from the dental mold to provide access to the free end of the dowel. Cap 40 has an internal recess 42 for snugly receiving the free end of the dowel 10. The cap 40 is bowl-shaped, with the outer end 44 being of larger diameter than the inner end 46, thereby facilitating its removal from the model or casting.

FIGS. 4A to 4D illustrate the manner in which my novel assembly is secured to the dental model. In each of these figures, there is shown only a portion of a master cast or a dental model which was made from a negative impression of a patient's mouth. For example, a drill 50 is used to drill a bore hole 52 into the top of the base 54 of the model which also contains a replica 56 of a prepared tooth. The dowel-pin 10 is then inserted and glued into the hole 52 (FIG. 4B), the locking device 22 inserted into the dowel-pin (FIG. 4C), and the plastic caps 40 and 32 inserted onto the ends of the dowel-pin and locking device, respectively (FIG. 4D). Each of FIGS. 4A-4D shows only a portion of the dental model, and it is to be understood that the dowel-pin and locking assembly is inserted in the top of each tooth model for which a restoration is to be fabricated.

FIGS. 5A to 5B show the same model portion with a wax box 60 formed therearound for containing a stone mix 62 which has been poured onto the entire top surface of the model to cover and embed the entire dowel-pin and locking assembly, including the locating caps 32 and 40. Again, it is emphasized that these drawing figures show only a portion of the dental model. After the stone mix has set, the model is trimmed by a conventional model trimmer (not shown) along the top surface until the outer surface of the locating cap 40 is engaged by the trimmer as indicated by the horizontal line 64. Similarly, the side of the model is trimmed until the trimmer exposes the locating cap 32 as indicated by the vertical line 66 in FIG. 5B. Then, and as illustrated in FIG. 5C, the caps 32 and 40 can be easily removed, thereby leaving in the dental stone respective recesses 32a and 40a which provide access to the extension 28 of the locking device 22 and to the free end 14 of dowel-pin 10, respectively. Before the stone mix 62 is poured, a lubricant may be placed on the upper surface 54a of the dental model in order to facilitate later removal of the tooth replica (die) from the stone base.

As shown in FIG. 6 after an individual tooth die has been defined by sawing on either side thereof in the dental model, the locking device 22 can be horizontally removed by means of a suitable instrument 70, and the tooth die, including the dowel-pin 10, can be vertically removed by tapping on the free end 14 thereof through the recess 40a. Of course, there remains in the dental stone 62 a cast recess 10a into which the dowel-pin 10 may later be re-inserted, and also recesses 24a and 26a into which the pins 24 and 26 of the locking device 22 may be reinserted.

FIGS. 7A and 7B show a larger portion 74 of a complete dental model of which the previous figures showed only a smaller portion. Here, saw cuts 76 and 78 have been made in the master cast or model 54 to isolate the tooth die 56 from the model. After these saw cuts are made, the locking device 22 is removed from the model, and the tooth die 56 is removed upwardly therefrom by tapping upwardly on the free end of the dowel-pin 10 which is exposed on the bottom of the model as viewed in FIGS. 7A and 7B. FIG. 7B shows a dental model in which several locking pins have been incorporated for different types of tooth restorations.

Thus, it can be seen that an individual locking device 22 is provided for each individual tooth die with its dowel-pin 10 containing the bore holes 18 and 20. Since the dental arch is arc-shaped, there is sufficient room for placement of the locking device 22 and its locating cap 32. The plastic locating caps 32 and 40 are designed to be disposable. The dowel pins 10 are seldom reused since the glue securing them usually incorporates a portion of the stone mix. However, the novel locking devices 22 may be reused, since they are not disturbed or damaged by any of the fabrication procedures described above.

FIGS. 8A and 8B illustrate the dimensions of a typical one of my novel dowel-pin and locking assemblies. The distance of 3.0 mm between the base of the dowel-pin and the top of the bore hole 18 is chosen to allow sufficient stone mix between the top surface of the upper locking pin 24 and the base of the dowel-pin (excluding the portion of the dowel-pin that is glued to the model). A spacing of approximately 3.0 mm between the bore holes 18 and 20 is chosen for the same reason. The diameters of the two bore holes and the corresponding legs of the locking device are chosen to accommodate the varying width of the dowel-pin due to its taper. The dimension of 7.50 mm from the bottom of the lower bore hole 20 to the free end 14 of the dowel-pin is non-critical except that there will be a lessened fulcrum effect of the die as the bore holes are placed closer to the top portion of the dowel-pin. Furthermore, and as shown in FIG. 8B, the pins 24 and 26 are preferably of equal length, and should be inserted through the corresponding bore holes of the dowel-pin 10 so that substantially equal lengths of the legs 24 and 26 are exposed on either side of the dowel-pin to allow for sufficient strength of the stone mix. The extension 28 of the locking device should be of sufficient length to approximate the outer rim of the dental model; excessive length may create a bulky model which may be difficult to trim. The height of the extension 28 is preferably less than the total height of both pins 24 and 26 of the locking device. The planar flange 30 is of sufficient size to seat against the stone model.

FIGS. 9A to 9D show different variations of the locking device 22. FIGS. 9A and 9B show knobs 80 and 82 for facilitating the grasping and removal of the locking device, FIG. 9C shows a cylindrical extension 84 having a hole therein for facilitating removal, and FIG. 9D shows a differently configured extension 86, all of these variations having a planar surface or flange for seating against the stone model.

FIG. 10C shows a simplified U-shaped locking pin 88 whose extension 90 is no larger than the diameter of the two cylindrical legs of the U; this locking device would be most economical, but the knob 82 in FIG. 9B is preferred. Regardless of the design of the grasping extension of the locking device, the pins or legs 24 and 26 are preferably straight cylindrical pins, i.e., are not tapered, so that the locking device does not have to be fully inserted through the dowel-pin at all times while still maintaining accuracy in the stabilization of the dowel-pin.

Since the anterior teeth are narrower than the posterior teeth, narrower dowel pins are utilized with a proportional reduction in the size of the locking device and its dual pins. Furthermore, the extension or pull portion of the locking device would be correspondingly narrower to accommodate the size of the dies. In this situation, this simple U-pin 88 of FIG. 10C would be preferred.

FIGS. 10A to 10E also show a variation utilizing this U-pin 88. FIG. 10A shows a narrower dowel-pin with correspondingly narrower cylinder bore holes. FIG. 10B shows a front view with the fastening pin 88 in a position; the width of the fastening pin is identical to the width or diameter of the cylindrical pins or legs of the U. FIG. 10D is a side view of the pin 88 inserted in a dowel-pin, and with a locating cap 92 fitted over the extension 90 of the pin 88. FIG. 10E shows a model 94 of (unprepared) anterior teeth. Numeral 1 identifies the locking device 88 in position (note that completely around the pin 88 is a recess which was formed by the plastic cap 92); numeral 2 refers to the bore holes left after the pin 88 has been removed from the stone model; and numerals 3 show the situation in which locking pins 88 have been removed, with the dotted lines marking areas of pin insertion in the stone model.

The length of the locking device pins 24 and 26, as illustrated in FIG. 8B, is approximately 9.0 mm. However, in practice, the optimum length would be longer. For example, when the locking device is placed in position in the dowel-pin, it should be positioned so that the locating cap is disposed approximately at the edge of the dental model, so that, when the model is trimmed, the plastic cap will be in the proper position for recovery. Because of such extra length of the pins, and because they are cylindrical rather than being tapered, they can be placed at will in the model at any desired position. Regardless of the variations of angles on the trimmed dental model, the locking pins will always be in the proper position.

Figure 11B:
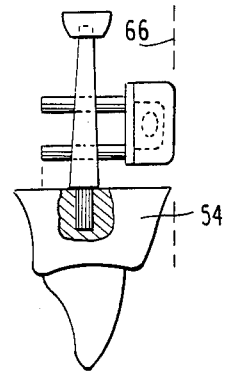
Figure 12A:
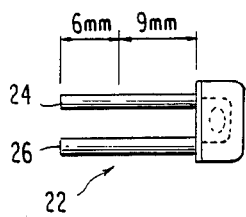
Figure 12B:
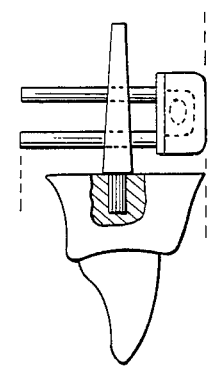
Figure 14A:
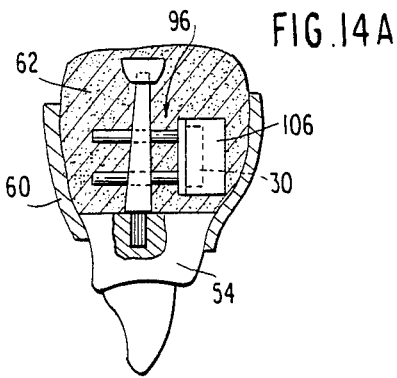

FIGS. 11A and 11B show the locking device having legs or pins 24, 26 with the length of approximately 9.0 mm. Note the position of the free ends of the pins relative to the edge of the dental model 54. For comparison, FIGS. 12A and 12B show a locking device whose pins are approximately 15 mm in length. Here, it is seen that the free ends of the pins extend beyond the edge of the model, but this is of no consequence, since the lingual area of the model will be filled with the stone mix.

Figure 13A:
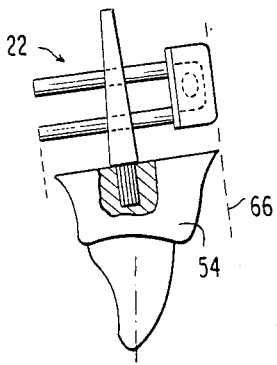
FIGS. 13A and 13B illustrate the efficacy of preferred embodiments of my invention.
Figure 14B:
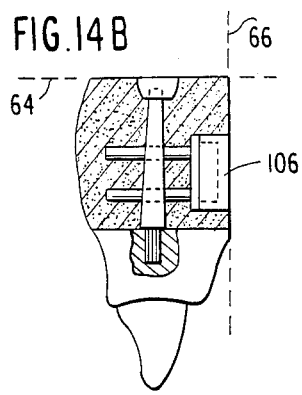
Figure 13B:
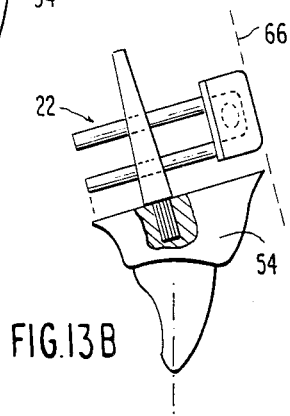

FIGS. 13A and 13B show dental models 54 with various widths and with various angles of model trimming, thereby showing that, regardless of such widths and angles, my novel locking device 22 may be placed in the proper locating position.

FIGS. 14A to 14E show another variation of a locking device 96 in which the flange 30 has a threaded hole 98 therein for subsequently receiving the threaded shank 100 of an extension or puller 102 having a knurled knob 104. In this case, the locking device 96, without the extension 102 but with a nylon cap 106 inserted over the flange 30, is embedded in the stone mix 62 (FIG. 14A), and, after trimming (FIG. 14B), the cap 106 is removed to expose the threaded flange 30 (FIG. 14C), so that the threaded extension 102 can be threaded therein (FIG. 14D) to permit the locking device 96 to be horizontally removed. FIG. 15E is a perspective view of this modified locking pin or device 96. With the use of this locking device 96, there is no fear of disturbing any extension thereon during trimming of the model, because of the greater distance between the flange 38 and the outer end of the plastic cap 106.

FIGS. 15A, 15B and 15C are similar to FIGS. 1A, 1B and 1C, respectively, and show a modification of my novel dowel-pin and locking assembly. Here, the dowel-pin 110 contains a longitudinally extending bore slot 112, rather than the two bore holes 18 and 20. The locking device 114 contains a single, essentially flat rod or pin 116 which is configured so that it will be snugly received by the slot 112 in the same manner that the bore holes 18 and 20 receive the cylindrical rods or pins 24 and 26. In this case, the elongated dimension of both the slot 112 and the rod 116 may be substantially equal to the distance between the top of bore hole 18 and the bottom of bore hole 20, thereby also to prevent movement in all directions of the tooth die or dowel-pin 110 when the locking device 114 is in position.

While various preferred embodiments of my invention have been described and illustrated above, it is to be understood that obvious modifications thereof may occur to those skilled in the art without departing from the spirit of the invention whose scope is to be measured only by the appended claims.

What is claimed is:

1. A tooth-die dowel-pin and locking assembly for locking only an individual tooth-die in a dental model against movement in all directions, comprising:

an elongated dowel-pin means adapted to be secured to the base of only an individual tooth die, said dowel-pin means having a free end and a fastening end;

said dowel-pin means having first hole means which extends transversely therethrough between opposite ends thereof and which has spaced apart hole portions; and locking pin means, having a free end and a grasping end, adapted to be transversely inserted through said first hole means and through corresponding mating second hole means in the base of a dental model, for locking said individual tooth die in the dental model against movement in all directions when said locking pin means is inserted through said first and second hole means, said first and second hole means being transversely aligned with each other when the tooth die is inserted in the dental model.

2. An assembly as defined in claim 1 wherein said first hole means comprises two first holes which are longitudinally spaced-apart by a distance, and wherein said locking pin means comprises a U-shaped pin having two legs which are spaced apart by said distance and whose free ends are respectively adapted to be transversely inserted through two corresponding mating second holes in the base of said dental model, said two first holes and said two second holes being transversely aligned with each other.

3. An assembly as defined in claim 2 wherein the opposite ends of said legs are joined by a planar flange means which is adapted to seat in a matching recess in the base of the dental model when said locking pin means is completely inserted in said first and second holes.

4. An assembly as defined in claim 2 wherein said first and second holes are circular holes and have substantially the same diameter, and wherein said legs are cylindrical and have said substantially same diameter.

5. An assembly as defined in claim 1 wherein said first hole means is a slot having a configuration of an elongation extending in the longitudinal direction of the dowel-pin means, and wherein said locking elongated pin means comprises a single elongated pin means, having substantially the same dimensions and configuration as said slot, for insertion through said slot and through a mating slot formed in the base of the dental model.

6. An assembly as defined in claim 1 further comprising machinable locating cap means on the free end of said dowel-pin means for locating said free end when said dowel-pin means is embedded in the dental model.

7. An assembly as defined in claim 1 further comprising extension means, on said grasping end of said locking pin means, adapted to be grasped when said locking pin means is to be removed from, and reinserted into, the dental model.

8. An assembly as defined in claim 7 further comprising machinable locating cap means on said extension means.

9. An assembly as defined in claim 7 wherein said extension means is integral with said locking pin means.

10. An assembly as defined in claim 9 wherein said extension means has an aperture therein for receiving an instrument to remove said pin means from the dental model.

11. An assembly as defined in claim 9 wherein said extension means is a knob.

12. An assembly as defined in claim 7 wherein said extension means is a removable threaded shank having a knob on an end thereof, and wherein said pulling end has a threaded hole for receiving said threaded shank.

13. An assembly as defined in claim 1, wherein said locking pin means for locking said individual tooth die against movement in all directions is of single-piece construction.

* * * * *